United States Patent
Weber et al.

(10) Patent No.: US 7,172,622 B2
(45) Date of Patent: Feb. 6, 2007

(54) MEDICAL DEVICES INCLUDING A MAGNETICALLY ACTIVATABLE BODY OR PORTION FOR TREATMENT

(75) Inventors: Jan Weber, Maple Grove, MN (US); Raed Rizq, Fridley, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 636 days.

(21) Appl. No.: 10/283,815

(22) Filed: Oct. 30, 2002

(65) Prior Publication Data

US 2004/0087899 A1    May 6, 2004

(51) Int. Cl.
*A61F 2/06*      (2006.01)
(52) U.S. Cl. ...................................... 623/1.12
(58) Field of Classification Search ............... 623/1.11, 623/1.12, 1.3, 1.16; 606/191–198, 108
See application file for complete search history.

(56) References Cited

U.S. PATENT DOCUMENTS

| | | | |
|---|---|---|---|
| 4,790,809 A | 12/1988 | Kuntz | 604/8 |
| 5,488,955 A | 2/1996 | Dias | 128/662.03 |
| 5,746,765 A * | 5/1998 | Kleshinski et al. | 128/898 |
| 5,851,218 A | 12/1998 | Lev | 606/198 |
| 5,882,338 A | 3/1999 | Gray | 604/131 |
| 5,928,261 A * | 7/1999 | Ruiz | 606/200 |
| 6,019,745 A | 2/2000 | Gray | 604/131 |
| 6,127,597 A * | 10/2000 | Beyar et al. | 606/86 |
| 6,157,101 A | 12/2000 | Ullakko | 310/26 |

OTHER PUBLICATIONS

Kakeshita, "Giant Magnetostriction in Ferromagnetic Shape-Memory Alloys", Materials Research Study Bulletin, Feb. 2002, vol. 27, No. 2, pp. 105-109.
O'Handley, "Phenomenology of giant magnetic-field-induced strain in ferromagnetic shape-memory materials", J. of Applied Physics, May 1, 2000, vol. 87, No. 9, pp. 4712-4717.
Murray, "6% magnetic-field-induced strain by twin-boundary motion in ferromagnetic Ni-Mn-Ga", J. of Applied Physics Letters, Aug. 7, 2000, vol. 77, No. 6, pp. 886-888.

* cited by examiner

*Primary Examiner*—Kevin T. Truong
(74) *Attorney, Agent, or Firm*—Brooks & Cameron, PLLC

(57) ABSTRACT

A medical device including an insertable body which is insertable into a body lumen or cavity. The insertable body of the medical device includes a magnetically activatable body portion to magnetically induce a dimension change to effect treatment.

16 Claims, 11 Drawing Sheets

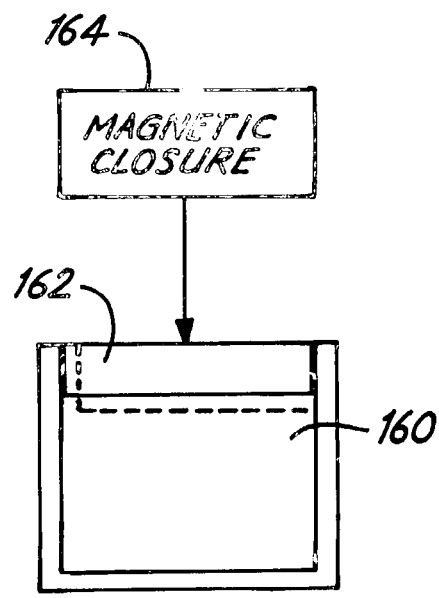
Fig. 10
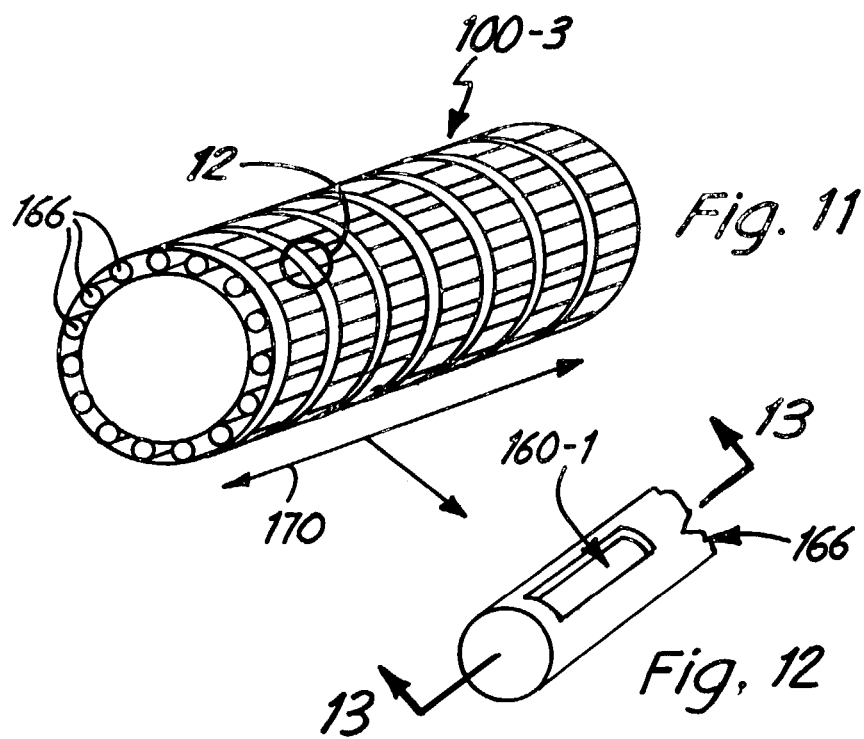
Fig. 11
Fig. 12

MEDICAL DEVICES INCLUDING A MAGNETICALLY ACTIVATABLE BODY OR PORTION FOR TREATMENT

BACKGROUND OF THE INVENTION

The present invention relates to medical devices. In particular, the present invention relates to medical devices including a magnetically activatable body or portion for medical treatment.

Various medical procedures involve placement of devices or instruments into a body lumen or cavity for medical treatment. The inserted device is manipulated externally for treatment. For example the device may includes an embolic device or stent which is radially deployed for treatment within a body cavity or lumen or alternatively, the device may include a treatment drug or agent which is deployed or dispensed. Deployment systems for such devices or agents are limited due to the internal or remote position of the treatment site. Embodiments of the present invention provide solutions to these and other problems, and offer advantages over the prior art.

SUMMARY OF THE INVENTION

The present invention relates to a medical device including an insertable body which is insertable into a body lumen or cavity. The insertable body of the medical device includes a magnetically activatable body portion to magnetically induce a dimension change to effect treatment.

BRIEF DESCRIPTION OF THE DRAWINGS

FIGS. 4-1 and 4-2 are cross-sectional illustrations taken generally along line 4-1, 4-2 -4-1, 4-2 of FIG. 3 illustrating an induced dimension change for magnetically deploying the stent.

FIG. 10 schematically illustrates an embodiment of a reservoir including a magnetically activatable closure.

FIG. 11 illustrates an embodiment of a stent including a reservoir cavity having a magnetically activatable closure as illustrated in detail in FIG. 12.

FIGS. 16-1, 16-2 and 17-1, 17-2 illustrate an embodiment of a magnetically activatable clamp for deploying an embolic device in which the embolic device is restrained as illustrated in FIGS. 16-1, 16-2 and released as illustrated in FIGS. 17-1, 17-2.

FIGS. 18-1 and 18-2 schematically illustrates an embodiment of an embolic coil or device having a constrained linear configuration and coiled unconstrained configuration.

DETAILED DESCRIPTION OF THE PREFERRED EMBODIMENTS

Various medical procedures involve placement or insertion of devices into a body cavity or lumen for treatment. Such devices are externally manipulated to position the devices at a remote site for treatment and include devices which are internally deployed at the treatment site. The present invention provides a magnetically activatable body or portion to magnetically activate, manipulate or deploy inserted devices for treatment.

Figure 1:
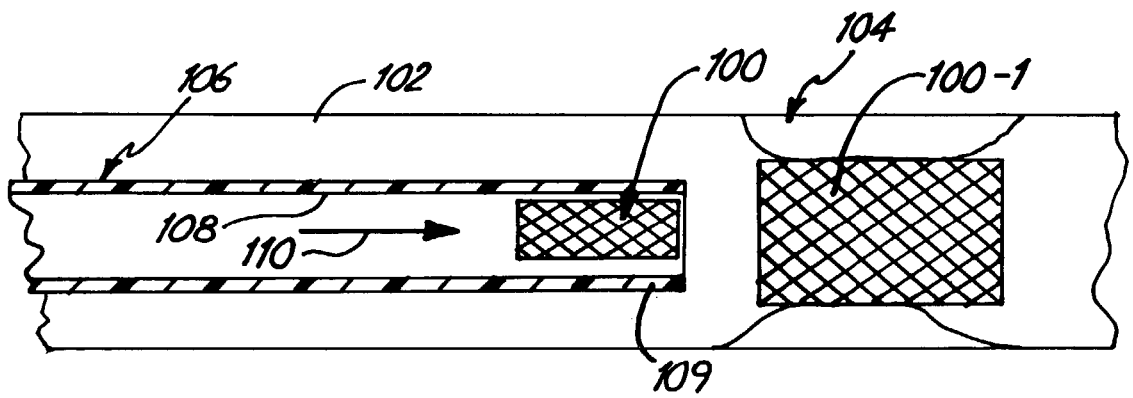
FIG. 1 schematically illustrates a prior art embodiment for deployment of a stent.

In particular, medical procedures for treating narrowing or obstructed blood vessels employ a deployable stent as illustrated in FIG. 1. As shown, the stent 100 is deployed in an obstructed body vessel or lumen 102 such as a coronary artery or vessel. The stent 100 is formed of a tubular body and is inserted through the body vessel or lumen 102 and advanced to a treatment site 104 proximate to the restriction by an elongated catheter 106. The stent 100 is disposed in an inner lumen 108 of the catheter 106 to maintain the stent 100 in a low profile for insertion.

In the illustrated embodiment the stent 100 is a self expanding stent 100 having a normally expanded profile. The normally expanded stent is mechanically constrained within the lumen 108 of the catheter 106 to provide the low profile for insertion. The stent 100 is advanced by advancing the catheter 106 to a deployment position spaced from the treatment site 104.

For deployment, the stent 100 is distally advanced from a distal end 109 of the catheter 106 to released the stent 100 from the catheter 106 and advance the stent 100 to the treatment site 104 as illustrated by arrow 110. Once the stent 100 is released from the catheter 106 the stent 100 expands to the normally expanded profile illustrated at 100-1 to treat the obstructed portion of the vessel or lumen 102. As described, the stent is advanced distally from the distal end 109 of the catheter 106 to the treatment site 104 rather than deployed "on-situs" at the treatment site 104.

I. Magnetically Deployable Stent or Device

Figure 2:
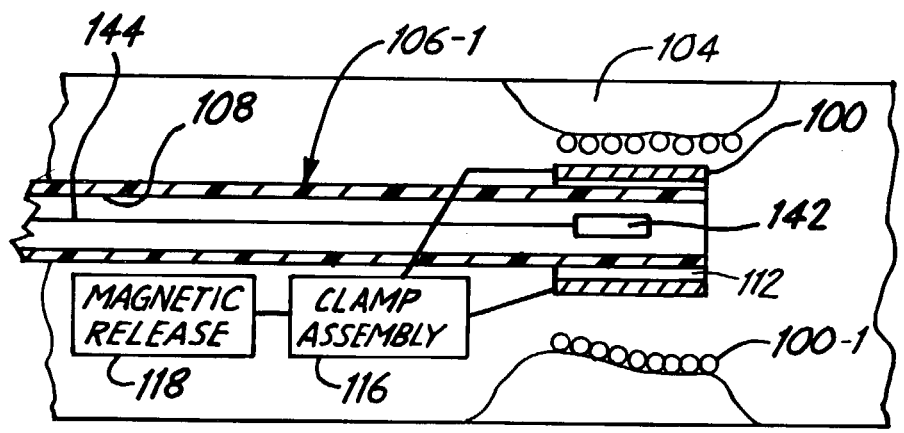
FIG. 2 schematically illustrates an embodiment for magnetically deploying a stent of the present invention.

The present invention provides an apparatus or assembly for "on-situs" deployment of a radially expandable treatment device such as a stent. FIG. 2 schematically illustrates an embodiment of an "on-situs" assembly for deployment of a stent or other treatment device where like numbers are used to refer to like parts in the previous FIGS. In the embodiment shown, the stent 100 is a normally expandable stent which is restrained in a collapsed dimension for insertion and magnetically released from the collapsed dimension to a radially expanded dimension 100-1 for use. The stent 100 is magnetically released by a magnetically induced dimension change of a clamping assembly for "on-situs" deployment of the stent 100.

In the embodiment illustrated in FIG. 2, the device or stent 100 is carried on a fixture 112 about an outer circumference of the catheter 106-1. The fixture 112 includes a magnetically activatable clamp assembly 116. The clamp assembly 116 normally maintains the stent 100 in the collapsed profile or dimension for insertion. A magnetic field is supplied as illustrated by block 118 to magnetically activate the clamp assembly 116 to release the stent 100 so that the stent expands to a normally expanded profile or dimension 100-1 for treatment. Thus, the device is inserted in a low profile for alignment with the treatment site 104 and magnetically released "on-situs" (at the treatment site 104) without temperature transformation or precise control as with shape memory alloy stents which expand relative to material transition temperatures.

Figure 3:
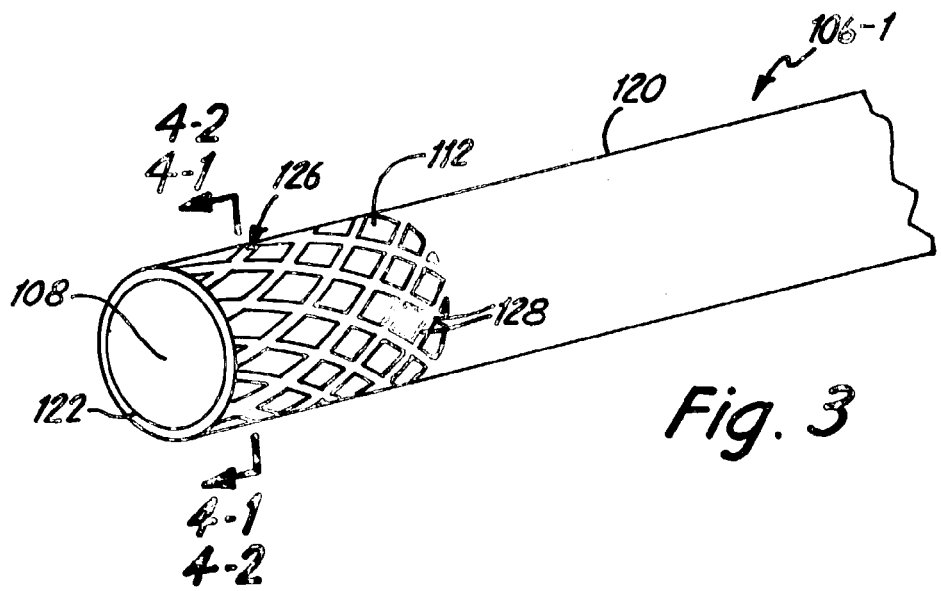
FIG. 3 schematically illustrates an embodiment of a catheter having a fixture for magnetically deploying a stent.
Figures 1, 4:
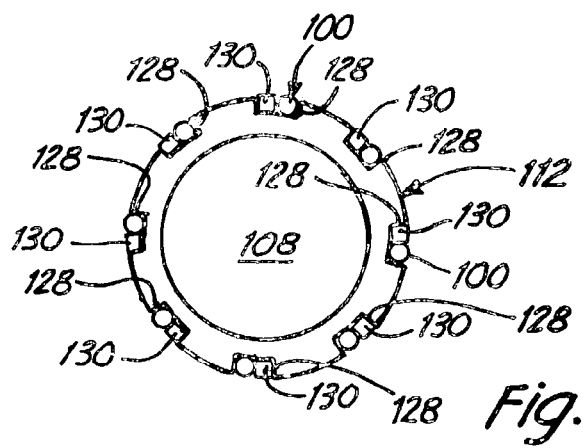
Figures 2, 4:
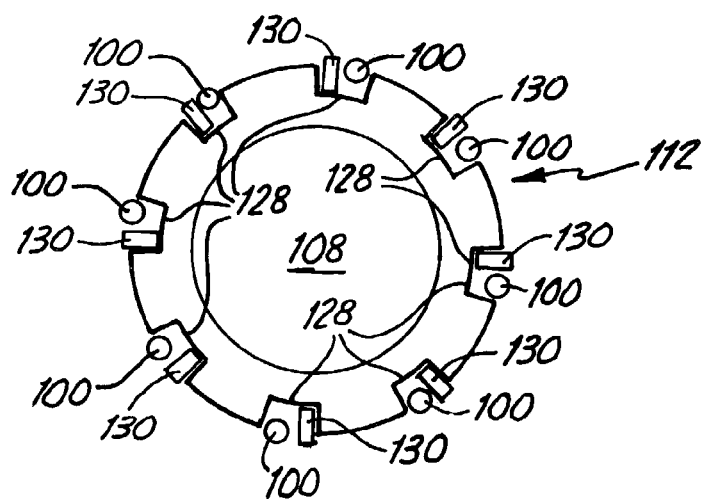

FIGS. 3–4 schematically illustrate an embodiment of fixture 112 including a magnetically activatable clamp assembly 116. As shown catheter 106-1 includes an elongated catheter shaft 120 having a proximal end, a distal end 122 and elongated lumen 108 therethrough. In the embodiment shown, the fixture 112 includes a negative pattern or lattice 126 along a distal portion of the catheter shaft 120. The negative pattern or lattice 126 forms a plurality of or pattern of channels 128 corresponding to the stent pattern. As shown in FIGS. 4-1 and 4-2, the channels 128 include a plurality of magnetically activatable bodies or portions 130. The magnetically activatable bodies or portions 130 are formed of material having magnetically induced dimension changes to form the magnetically activatable clamp assembly 116. Although a particular pattern or lattice is shown, application is not limited to the specific pattern shown and alternate patterns may be used depending upon the stent pattern or configuration.

In the illustrated embodiment, the magnetically activatable bodies or portions 130 are formed of a ferromagnetic shape memory alloy (FMSA) such as $Ni_2MnGa$ having a twin variant crystalline structure. In particular, the bodies 130 are formed of a twin variant crystal structure in a martensite phase having a martensite temperature within the temperature range of the body. By applying a magnetic field in one of the mirror variants or easy axes, the magnetic field will tend to align the magnetic moments so that one crystal twin shears into the other mirror variant to induce a dimension change or strain. As shown with reference to FIGS. 4-1 and 4-2, the magnetically activatable dimension change or strain is used to retain or wedge the stent 100 in the negative pattern 126 or channels 128 as shown in FIG. 4-1 and to release or deploy the stent as shown in FIG. 4-2.

Figure 5:
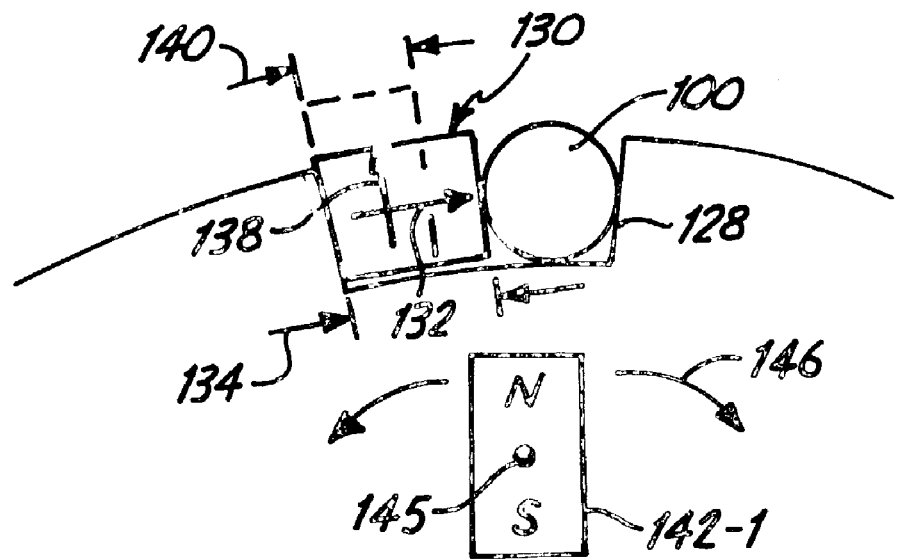
FIGS. 5–6 are detailed illustrations of alternate embodiments for magnetically deploying a stent.

As shown in detail in FIG. 5, the magnetically activatable bodies 130 are disposed in channels 128. For insertion, the magnetically activatable bodies 130 are sized to retain the stent 100 in the channels 128 and the bodies 130 have a magnetically induced dimension change to release the stent 100 for deployment. In the embodiment illustrated in FIG. 5, the bodies 130 are stressed along a first easy axis 132 to provide a first radial dimension 134 and a magnetic field is supplied along a second mirror easy axis 138 to provide a second smaller radial dimension 140 to release the stent 100 from channel 128. Although particular variant axes 132, 138 are shown for illustration, application is not limited to the particular orientation or 90° angle between axis 132, 138.

In one embodiment, the magnetic field can be supplied by an internal or external radially orientated magnetic field using a permanent magnet (such as a neodymium iron boron magnet—Nd—Fe—B) or an electromagnet. The internal field can be supplied by a magnet device 142 (permanent magnet or electromagnet) coupled to or embedded along an elongated shaft 144 which is insertable through the lumen 108 of the catheter 106-1 as illustrated in FIG. 2. Depending upon the material, field strengths greater than 0.1 Telsa provide transformation of the crystal structure and 100% transformation occurs at 1–2 Telsa. As described, application of the magnetic fields in the variant or easy axes can produce strains in the range of 6%.

Figure 6:
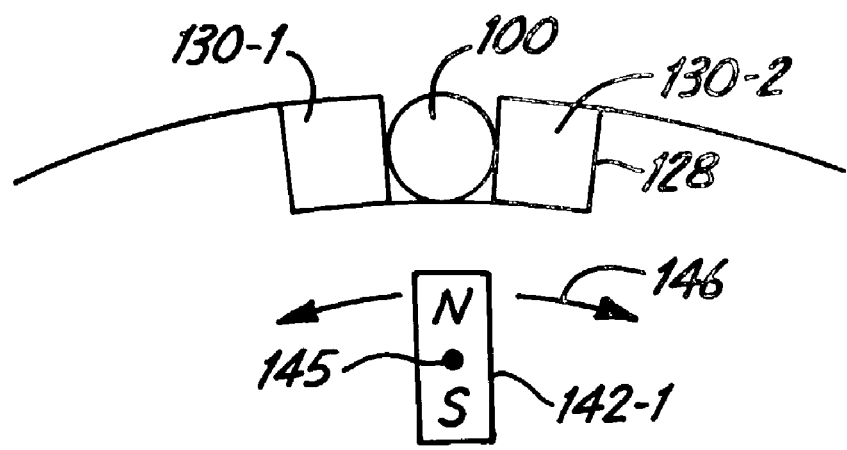

FIGS. 5–6 illustrate an embodiment of magnetic device 142-1 having a magnet (permanent or electromagnetic) orientated generally perpendicular to a longitudinal axis 145 to provide a magnetic field along axis 138. Rotation of the internal magnet or magnetic field as illustrated by arrow 146 in FIGS. 5–6 sequentially induces a radial dimension change for the activation bodies 130 about the circumference of the fixture 112 to progressively release the stent 100. Once the stent is released by the clamp assembly 116, the stent 100 self expands for treatment. In an alternate embodiment, the bodies can be magnetically activated externally to release the stent or expandable device for deployment.

FIG. 6 illustrates an alternate structure including opposed activatable bodies 130-1, 130-2 to retain the stent in the channels 128 therebetween. As previously described, the opposed activatable bodies 130-1, 130-2 are similarly activated to induce a dimension change to release the stent for treatment. The channels or pattern of the fixture 112 can be formed in the catheter shaft using a laser etching process. Thus, as described, the stent is magnetically deployed "on-situs" for desired placement of the stent.

Although application of the "on-situs" deployment structure is described with respect to a radially expandable stent, application extends to other radially expandable devices deployed in a body lumen or cavity such as expandable filters or embolization structures. Although application of the magnetically activatable deployment is illustrated with respect to a particular stent embodiment or design, it should be understood that application is not limited to any particular stent embodiment or design.

II. Magnetically Activatable Drug Delivery

Figure 7:
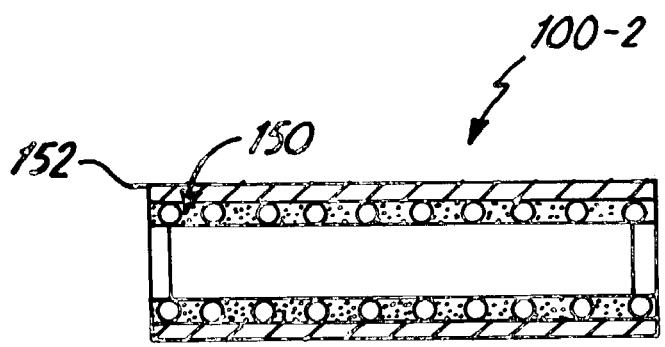
FIGS. 7–8 cooperatively illustrate drug or therapeutic agent delivery using a coated stent.
Figure 8:
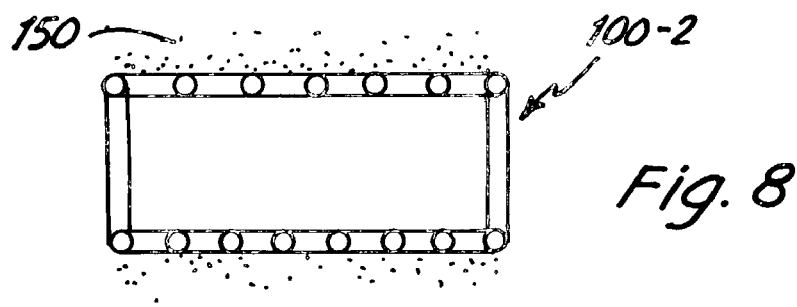
Figure 9:
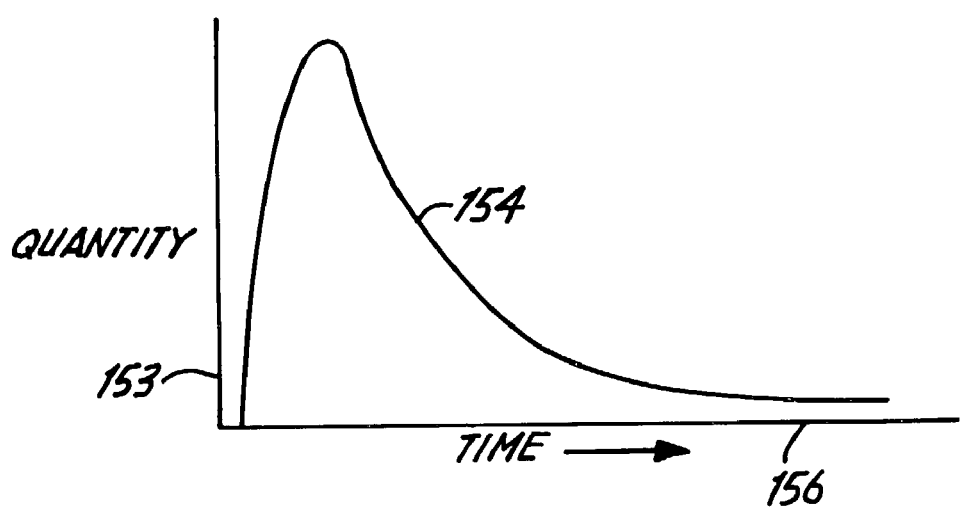
FIG. 9 graphically illustrates drug or agent concentration for a coated stent.

Medical treatment procedures also include "on-situs" delivery of drugs or therapeutic agents for treatment. Application of the present invention provides for magnetically activatable drug delivery for a therapeutic agent or drug at a remote treatment site within a body lumen or cavity. For example, stents and other devices coated with a therapeutic agent, such as anticoagulants or thrombolitic agents provide drug delivery for site specific application of drugs as shown in FIGS. 7–8. As shown coated stent 100-2 includes a drug or agent 150 interspersed in a polymer coating 152 on the stent 100-2. Upon radial expansion of the stent 100-2, the polymer coating 152 is expanded to release the drug or agent 150 for treatment as illustrated in FIG. 8. Thus, as shown in FIG. 9, a quantity (as illustrated by axis 153) of drug or agent 154 is released upon deployment of the stent to provide drug treatment for a period of time following deployment of the stent 100-2 as illustrated by axis 156.

The present invention provides a magnetically activatable drug delivery system for delivery of a drug or agent in a body lumen or cavity. In the embodiment schematically illustrated in FIG. 10, the device includes a drug or agent reservoir cavity 160 having a magnetically activatable reservoir closure 162 which is magnetically activatable as illustrated by block 164 to open (as illustrated by the dotted line) the closed reservoir cavity 160 to release a drug or agent. In the illustrated embodiment, reservoir closure 162 is formed of a material having a twin variant crystalline structure having a magnetically inducible dimension change.

Figure 13:
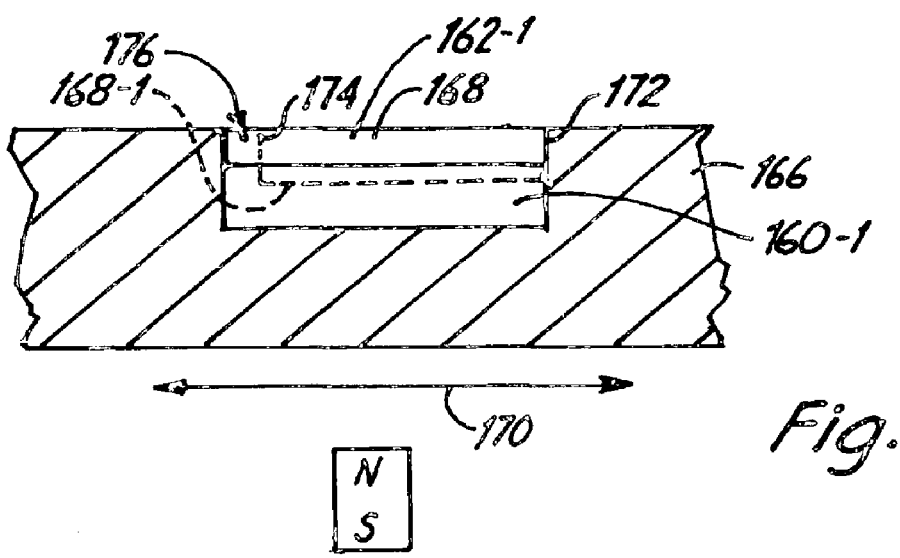
FIG. 13 is a cross-sectional view taken along line 13—13 of FIG. 12 illustrating the reservoir cavity and magnetically activatable closure therefor.

The magnetically activatable drug delivery system is embodied in a stent 100-3 in the embodiment illustrated in FIGS. 11-13. Stent 100-3 includes a plurality of reservoir cavities 160-1 laser etched or formed in stent filaments 166 forming the tubular stent body. The plurality of reservoir cavities 160-1 are filled with the desired drug or agent and are closed by a magnetically activatable reservoir closure 162-1 as shown in FIG. 13. Application of the magnetically activatable delivery system as described provides for "on-situs" drug treatment which is activated independent from deployment of the stent 100 or other deployable device.

Reservoir closure 162-1 includes a reservoir closure body 168 formed of a FMSA having a twin mirror variant crystalline structure which has an activatable dimension change by supplying a magnetic field along one of the easy axes to transform the crystal structure of the body from a first crystal structure to a mirror structure to induce the dimension change. In the embodiment illustrated in FIG. 13, the reservoir closure body 168 is orientated to provide a longitudinal dimension change along a longitudinal or axial length 170 of the stent 100-3, although application is not limited to the particular longitudinal orientation described. In one embodiment, the reservoir closure body 168 is stressed along a first longitudinal direction to provide an elongated dimension. A magnetic field is supplied in a second mirror orientation to provide a second shortened dimension as illustrated by dotted lines 168-1 to release drug or agent from the reservoir cavity 160-1.

In the particular embodiment shown, the reservoir closure body 168 includes a fixed end 172 and a floating end 174 and is magnetically activated to provide a gap 176 between the reservoir closure body 168 and a surface of the reservoir cavity 160-1 to release the drug or agent. As previously described, the magnetic field can be internally supplied by inserting a magnetic device such as a permanent magnet or electromagnet through the body lumen or vessel to the treatment site or can be externally supplied.

Figure 14:
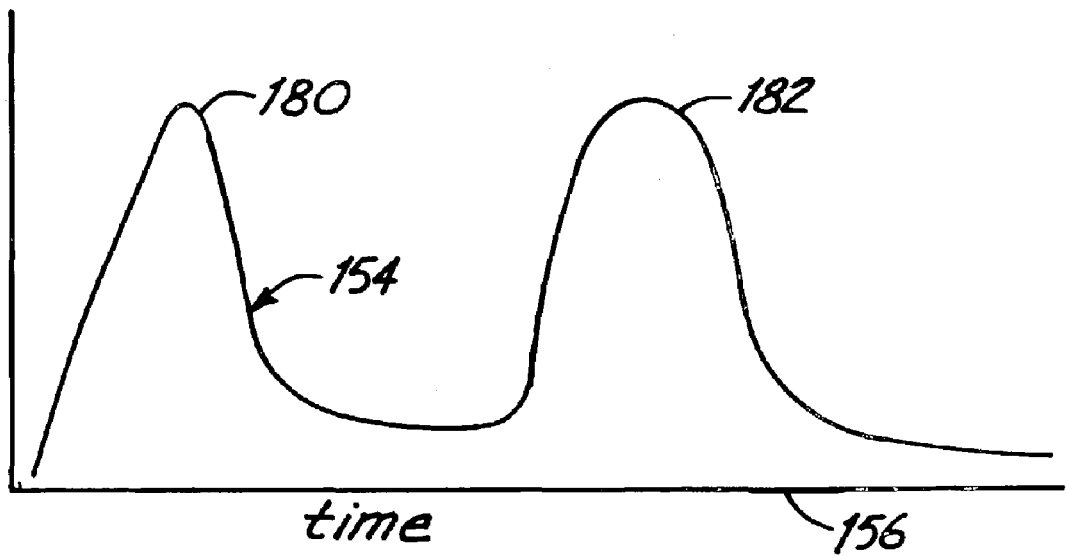
FIG. 14 graphically illustrates drug or agent treatment concentrations for delivery of multiple doses using a coated stent and a magnetically activatable system.

As described, coated stents provide dispersement or delivery of a treatment dosage of a therapeutic agent or drug upon deployment of a stent. A magnetically activatable delivery system described with respect to stent 100-3 can be used with a coated stent. In particular as illustrated in FIG. 14, the coated stent and magnetically activatable delivery system provides a first treatment dosage 180 upon deployment of a stent and a second magnetically activatable dosage 182 to increase the dosage or drug treatment period.

Figure 15:
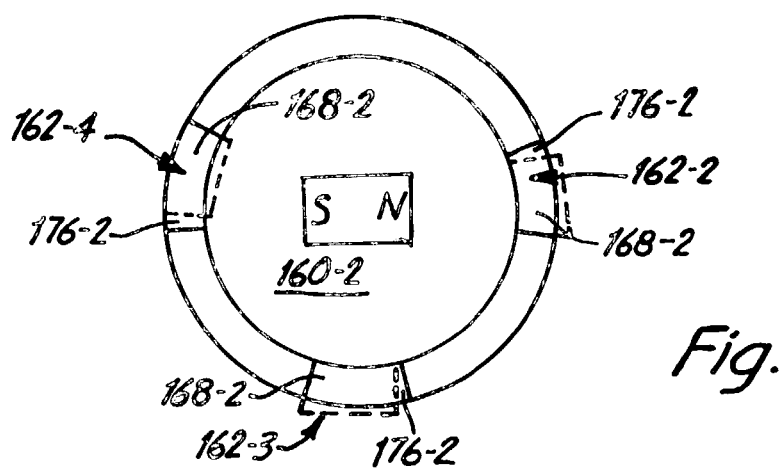
FIG. 15 illustrates an alternate embodiment of a reservoir cavity and magnetically activatable closure.
Figures 1, 16:
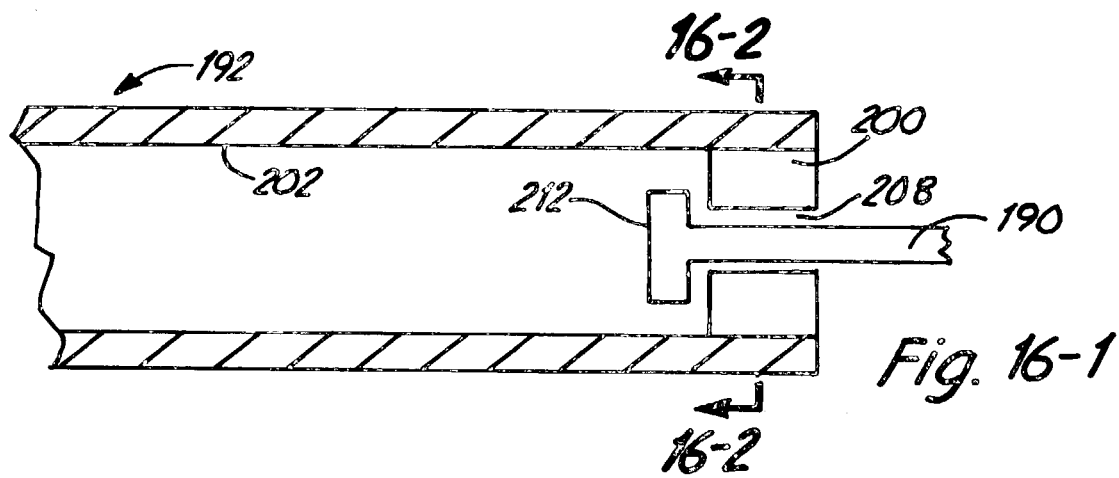
Figures 2, 16:
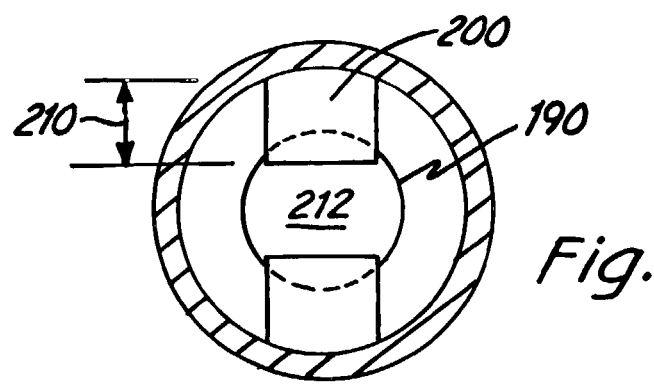

In an alternate embodiment illustrated in FIG. 15, the reservoir cavity 160-2 is formed in a tubular device and magnetically activatable reservoir closures 162-2, 162-3, 162-4 are radially spaced thereabout to release a drug or agent for treatment. The reservoir closures include magnetically activatable closure bodies 168-2 as previously described which are activatable to selectively release drug from the reservoir cavity 160-2 through gap or openings 176-2. In particular, as shown, a rotating magnetic field is supplied to progressively activate the radially spaced reservoir closures 162-2, 162-3, 162-4 to radially dispense a therapeutic drug or agent.

III. Magnetically Deployable Embolic Device or Coil

For treatment of aneurysms or other body distensions, thrombolic devices or coils 190 are deployed. Thrombolic devices or coils 190 are typically delivered through a catheter for placement at the treatment site. FIGS. 16-1, 16-2 and 17-1, 17-2 illustrate an embodiment of a magnetically activatable clamp assembly to magnetically deploy or release a device or coil 190 for treatment from a delivery catheter 192. As illustrated, the clamp assembly includes a magnetically activatable clamp body 200 having a magnetically activatable dimension change as previously described.

In the illustrated embodiment, the body 200 is disposed in an inner lumen 202 of a delivery catheter 204. In the illustrated embodiment, body 200 is formed of a twin variant crystalline structure having an actuatable dimension change to provide an adjustable opening 208 to the inner lumen 202 of the catheter 192. In the particular embodiment shown, clamp body 200 includes an adjustable radial thickness dimension 210 as comparatively illustrated in FIGS. 16-2 and 17-2 to provide a magnetically activatable adjustable opening 208 dimension.

Figures 1, 17:
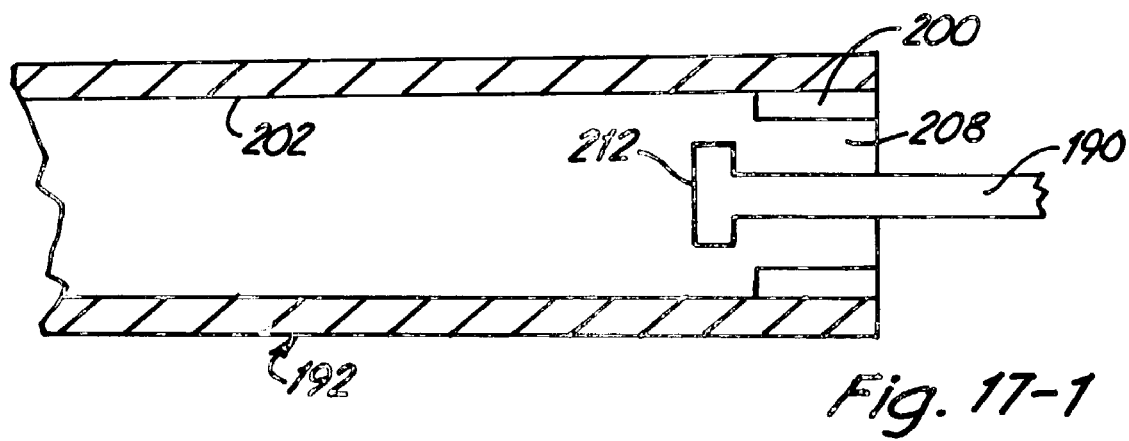
Figures 2, 17:
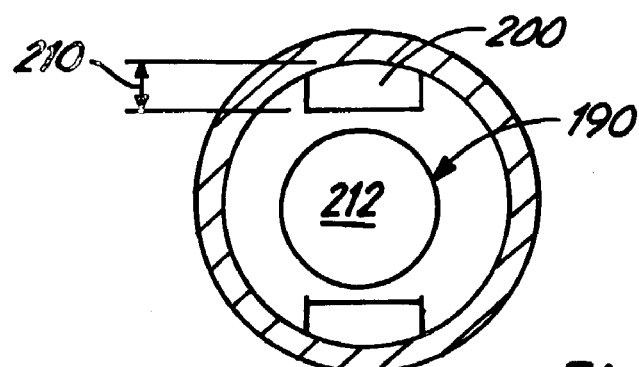

The embolic coil or device 190 includes a low profile for insertion through lumen 202 of the catheter 192 for placement at the treatment site and is expanded for deployment for treatment. The embolic coil or device 190 includes a bulbous or enlarged end portion 212 which has a larger dimension than the opening dimension 208 prior to activation. The clamp body 200 is activatable to a smaller radial thickness dimension than the bulbous or enlarged end portion 212 of the embolic device as illustrated in FIG. 17-2 to release the embolic device for treatment.

In particular, in the embodiment shown, clamp body 200 is prestressed in the radial direction along a first twin variant to provide a first radial thickness and a magnetic field is supplied along a second twin variant to provide a smaller radial thickness to deploy the device. The clamp body 200 can be activated as previously described using an internally inserted magnetic device which is inserted through lumen 202 of the catheter 192 or an external device which supplies an external magnetic field.

Figures 1, 18:
Figures 2, 18:
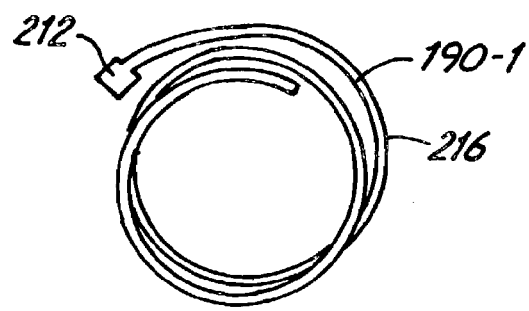

In one embodiment illustrated in FIGS. 18-1 and 18-2, device or coil 190-1 includes a coiled wire or filament having a constrained linear configuration 214 to provide a low profile dimension for insertion and a coiled unconstrained configuration 216 for treatment or deployment. Although particular embodiments are illustrated, application is not limited to the specific embodiments shown for example, in one embodiment, the clamp assembly includes multiple spaced clamp bodies and application is not limited to any particular actuation orientation or particular position or location of the magnetically activatable clamp body 200 along the catheter 192.

IV. Magnetically Activatable Steering

The treatment devices described and other treatment devices are advanced by steering and advancing the device through a body lumen, cavity or vessel. For example, cardiac catheters or devices are inserted in a femoral artery and are steered through a patient's vasculature to a cardiac treatment site. The path through which the catheter is steered is tortuous and curved and the catheter must be sufficiently pushable and flexible to steer through the tortuous path.

Figure 19:
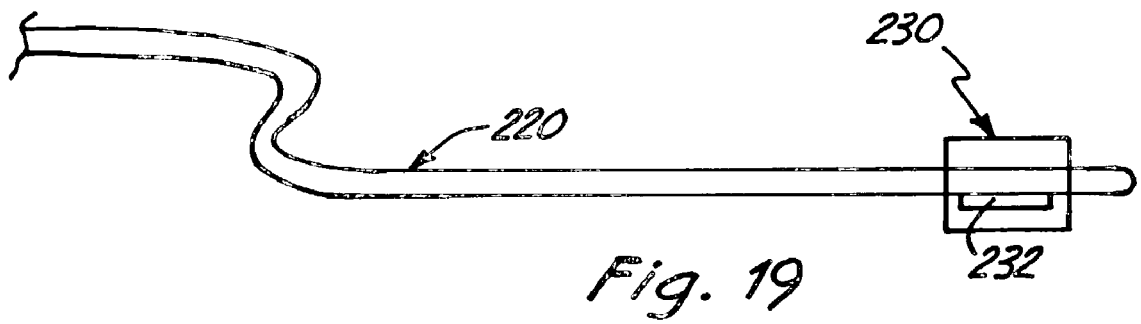
FIG. 19 schematically illustrates an embodiment of a catheter including a magnetically activatable steering portion or body.
Figure 20:
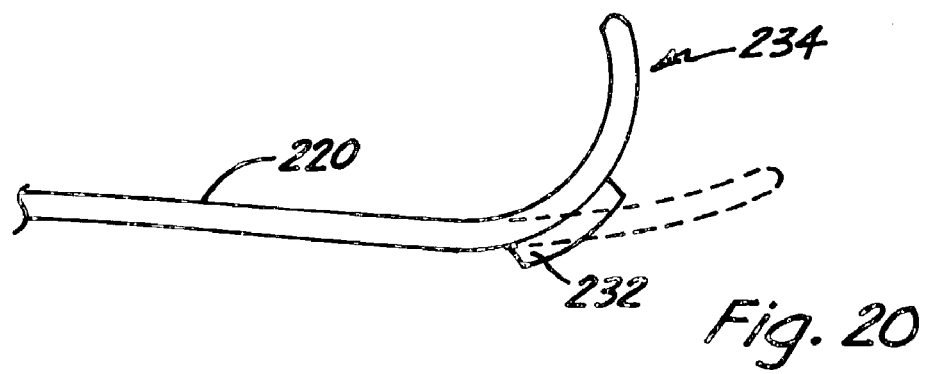
FIG. 20 schematically illustrates a catheter having a preformed tip including a magnetically activatable steering portion.

FIG. 19 illustrates an embodiment of a catheter 220 including a magnetically activatable steering device 230 along a portion of the catheter 220 to adjust a curvature of a distal tip or portion of the catheter for steering. The magnetically activatable steering device as illustrated in FIG. 19 includes at least one magnetically activatable steering body 232 formed of material having a twin variant crystalline structure having a magnetically activatable dimension change. In one illustrated embodiment shown, the magnetically activatable steering body 232 is bent to provide a normally bent tip 234 or distal portion and is magnetically activatable to relax or straighten the normally bent tip or distal portion 234. Alternatively, the magnetically activatable body 232 can have an adjustable linear dimension along an elongated length of the catheter 220 to adjust or straighten a normally bent tip or distal portion 234.

Figure 21:
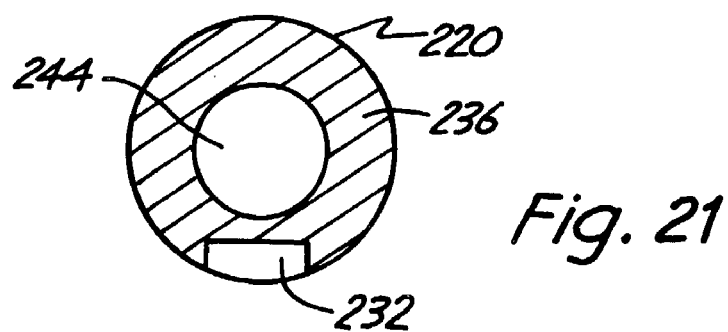
FIG. 21 is a cross-sectional view of a catheter having a recessed magnetically activatable steering portion or body.

In an alternate embodiment, the steering body 232 is magnetically activated to provide a curvature or bend to the catheter tip or portion of the catheter by activating a linear dimension change. The magnitude of the magnetic field supplied to activate the steering body 232 can be adjusted based upon the desired curvature. As illustrated in FIG. 21, in one embodiment, the steering body 232 can be embedded or recessed in a catheter wall 236 to provide a low profile for insertion and treatment.

Figure 22:
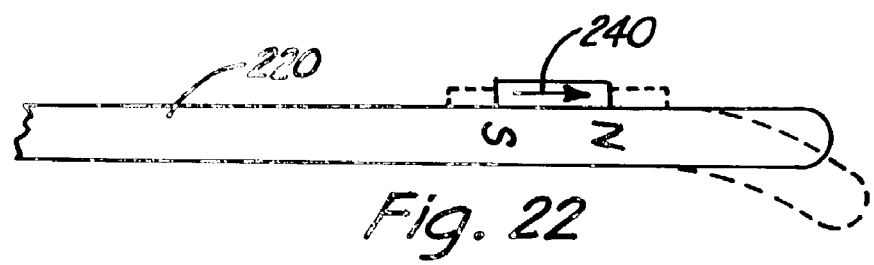
FIGS. 22–23 illustrate an embodiment of a catheter including bidirectional steering.
Figure 23:
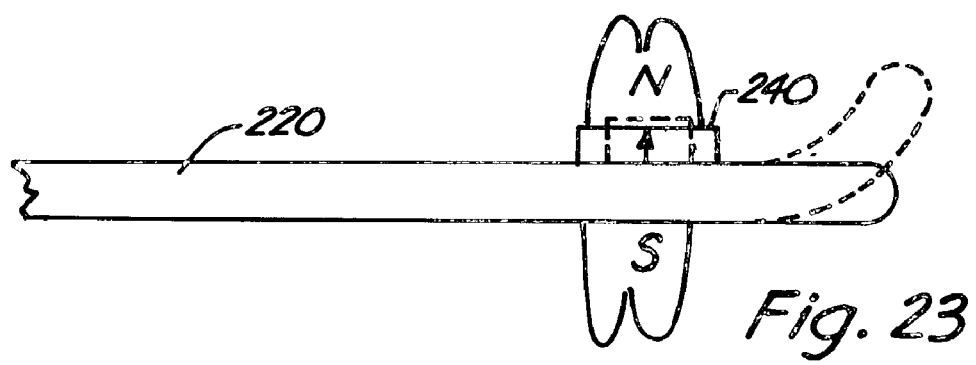
Figure 24:
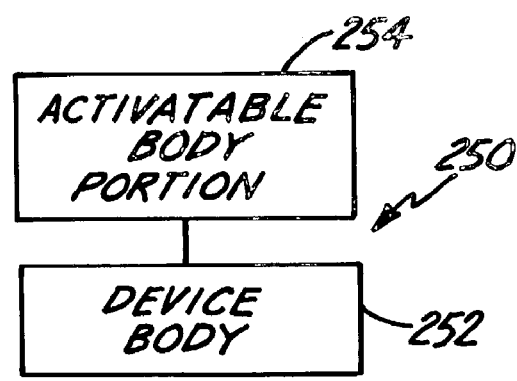
FIG. 24 schematically illustrates a medical device including a magnetically activatable body or portion for treatment.

In the embodiment illustrated in FIGS. 22–23 the catheter 220 includes a magnetically activatable bi-directional steering assembly where like numbers are used to refer to like parts in the previous FIGS. In the embodiment shown, the steering assembly includes a magnetically activatable steering body 240 similarly formed of a twin variant crystalline structure. As comparatively shown in FIGS. 22–23, magnetic fields are supplied to the body 240 in opposed directions to induce opposed dimension changes to bidirectionally bend the catheter.

In particular, a magnetic field is supplied along a first mirror variant to increase a linear dimension to bend the catheter in a first direction and a magnetic field is supplied along a second mirror variant to decrease the linear dimension to bend the catheter in a second direction to steer the catheter. As previously described, the magnetic field can be externally or internally supplied by advancing a magnetic device through a lumen 244 (as illustrated in FIG. 21) of the catheter as previously described. Thus, as described, the invention provides a medical device 250 including a device body 252 having a magnetically activatable body portion 254 to effect treatment.

Although the present invention has been described with reference to preferred embodiments, workers skilled in the art will recognize that changes may be made in form and detail without departing from the spirit and scope of the invention.

What is claimed is:

1. A medical device comprising:
   an insertable body insertable into a body lumen or cavity including a magnetically activatable body portion formed of a material having a twin variant crystalline structure having a magnetically activatable dimension change.

2. The medical device of claim 1 wherein the insertable body includes an elongated catheter and the activatable body portion is along a portion of the elongated catheter.

3. The medical device of claim 2 wherein the insertable body includes a radially expandable stent and the activatable body portion is disposed on the stent.

4. In combination:
   an elongated catheter; and
   a magnetically activatable body formed of a material having a twin variant crystalline structure having a magnetically activatable dimension change.

5. The combination of claim 4 and further comprising:
   an elongated shaft having a magnetic device coupled thereto to magnetically activate the dimension change.

6. A medical device comprising:
   an expandable stent having a normally expandable radial dimension and a collapsible radial dimension; and
   a catheter including a fixture about an outer circumference thereof and the fixture including a magnetically activatable clamp assembly to restrain the stent in the collapsible radial dimension for insertion and magnetically activatable to release the stent for deployment.

7. The device of claim 6 wherein the magnetically activatable clamp assembly includes a magnetically activatable body having a magnetically activatable dimension change.

8. The device of claim 7 wherein the magnetically activatable body is formed of a material having a twin variant crystalline structure.

9. The medical device of claim 6 wherein the fixture includes:
   a pattern of channels about the outer circumference of the catheter and the stent being disposed in the channels and the magnetically activatable clamp assembly includes:
   a plurality of magnetically activatable bodies having a magnetically activatable dimension change disposed in the channels to restrain the stent in the channels and selectively activatable to release the stent from the channels for deployment.

10. A method for deploying a stent comprising steps of:
    positioning a stent proximate to a treatment site in a collapsed profile; and
    supplying a magnetic field to cause a dimensional change in magnetically activatable bodies to magnetically release the stent from the collapsed profile to deploy the stent.

11. The method of claim 10 wherein the step of supplying a magnetic field to deploy the stent comprises:
    aligning a magnetic device relative the stent; and
    rotating the magnetic device to supply the magnetic field to deploy the stent.

12. The method of claim 11 wherein the stent is supported along an elongated catheter to position the stent proximate to the treatment site and the step of aligning the magnetic device relative to the stent comprises:
    inserting the magnetic device through a lumen of the catheter and advancing the magnetic device to align with the stent at the treatment site; and
    rotating the magnetic device within the lumen of the catheter to deploy the stent.

13. The method of claim 12 wherein the stent is supported by a fixture including a pattern of channels on the elongated catheter and the stent is restrained in the pattern of channels by a plurality of the magnetically activatable bodies formed of a material having a twin variant crystalline structure and comprising the step of:
    magnetically activating the dimension change in the plurality of the activatable bodies to release the stent from the pattern of channels.

14. A method for deploying a treatment device comprising steps of:
    inserting the treatment device into a body vessel or cavity and positioning the treatment device at a treatment site; and
    magnetically inducing a dimension change in a magnetically activatable body to magnetically deploy the treatment device.

15. The method of claim 14 wherein the treatment device is one of a stent or an embolic device.

16. The method of claim 14 including intravascularly inserting the treatment device with an elongated catheter, where the catheter includes the magnetically activatable body that undergoes the dimension change to deploy the treatment device.

* * * * *